(12) United States Patent
Perry

(10) Patent No.: US 9,795,418 B2
(45) Date of Patent: Oct. 24, 2017

(54) SYSTEMS AND METHODS FOR SPINAL COMPRESSION, DISTRACTION, AND FIXATION

(71) Applicant: Alphatec Spine, Inc., Carlsbad, CA (US)

(72) Inventor: Thomas Perry, Vista, CA (US)

(73) Assignee: Alphatec Spine, Inc., Carlsbad, CA (US)

( * ) Notice: Subject to any disclaimer, the term of this patent is extended or adjusted under 35 U.S.C. 154(b) by 375 days.

(21) Appl. No.: 14/192,502

(22) Filed: Feb. 27, 2014

(65) Prior Publication Data

US 2014/0277154 A1    Sep. 18, 2014

Related U.S. Application Data

(60) Provisional application No. 61/789,146, filed on Mar. 15, 2013.

(51) Int. Cl.
*A61B 17/70* (2006.01)
*A61B 17/80* (2006.01)

(52) U.S. Cl.
CPC ...... *A61B 17/7044* (2013.01); *A61B 17/7049* (2013.01); *A61B 17/7059* (2013.01); *A61B 17/8042* (2013.01); *A61B 17/7032* (2013.01); *A61B 17/809* (2013.01)

(58) Field of Classification Search
CPC ............ A61B 17/7032; A61B 17/7034; A61B 17/7035; A61B 17/7041; A61B 17/7043; A61B 17/705; A61B 17/7044; A61B 17/7049–17/7052; A61B 17/7059; A61B 17/7019; A61B 17/7025

USPC .......................................................... 606/270
See application file for complete search history.

(56) References Cited

U.S. PATENT DOCUMENTS

| | | | | |
|---|---|---|---|---|
| 4,696,290 A | * | 9/1987 | Steffee | A61B 17/7059 606/280 |
| 5,603,714 A | * | 2/1997 | Kaneda | A61B 17/7034 606/272 |
| 6,355,038 B1 | * | 3/2002 | Pisharodi | A61B 17/7043 411/538 |
| 2007/0233091 A1 | * | 10/2007 | Naifeh | A61B 17/7005 606/279 |
| 2008/0097448 A1 | * | 4/2008 | Binder | A61B 17/7007 606/74 |
| 2010/0125299 A1 | * | 5/2010 | Paul | A61B 17/7055 606/280 |
| 2010/0222825 A1 | * | 9/2010 | Paul | A61B 17/7055 606/280 |

(Continued)

*Primary Examiner* — Jacqueline Johanas
*Assistant Examiner* — Tessa Matthews
(74) *Attorney, Agent, or Firm* — Dinsmore & Shohl LLP

(57) ABSTRACT

An apparatus for coupling with a fixation rod to allow spinal compression, distraction, and fixation along an antero-lateral aspect of a spine includes an elongated plate, first and second fixation screws, and a first arm. The elongated plate includes a first aperture at a superior end and a second aperture at an inferior end. The first fixation screw is received by the first aperture and engages a first body portion of a first vertebra. The second fixation screw is received by the second aperture and engages a second body portion of a second vertebra. The first arm extends transversely from a first base portion on the elongated plate and includes a first hook to couple with a first portion of the fixation rod.

5 Claims, 5 Drawing Sheets

(56) References Cited

U.S. PATENT DOCUMENTS

2011/0106164 A1\* 5/2011 Wilcox .............. A61B 17/7041
606/264

\* cited by examiner

SYSTEMS AND METHODS FOR SPINAL COMPRESSION, DISTRACTION, AND FIXATION

CROSS-REFERENCE TO RELATED APPLICATIONS

The present application claims priority to U.S. Provisional Application Ser. No. 61/789,146 entitled "Hybrid Antero-Lateral Plate and Kaneda System" which was filed on Mar. 15, 2013 and is incorporated herein by reference in its entirety.

FIELD

The present disclosure generally relates to the field of spinal orthopedics, and more particularly to systems and methods for spinal compression, distraction, and fixation from an antero-lateral or lateral approach.

BACKGROUND

The spine is a flexible column formed of a plurality of bones called vertebrae. The vertebrae are hollow and piled one upon the other, forming a strong hollow column for support of the cranium and trunk. The hollow core of the spine houses and protects the nerves of the spinal cord. The different vertebrae are connected to one another by means of articular processes and intervertebral, fibrocartilaginous bodies. Various spinal disorders may cause the spine to become misaligned, curved, and/or twisted or result in fractured and/or compressed vertebrae. It is often necessary to surgically correct these spinal disorders.

The spine includes seven cervical (neck) vertebrae, twelve thoracic (chest) vertebrae, five lumbar (lower back) vertebrae, and the fused vertebrae in the sacrum and coccyx that help to form the hip region. While the shapes of individual vertebrae differ among these regions, each is essentially a short hollow shaft containing the bundle of nerves known as the spinal cord. Individual nerves, such as those carrying messages to the arms or legs, enter and exit the spinal cord through gaps between vertebrae.

The spinal disks act as shock absorbers, cushioning the spine, and preventing individual bones from contacting each other. Disks also help to hold the vertebrae together. The weight of the upper body is transferred through the spine to the hips and the legs. The spine is held upright through the work of the back muscles, which are attached to the vertebrae. While the normal spine has no side-to-side curve, it does have a series of front-to-back curves, giving it a gentle "S" shape. If the proper shaping and/or curvature are not present due to scoliosis, neuromuscular disease, cerebral palsy, or other disorder, it may be necessary to straighten or adjust the spine into a proper curvature.

In some instances, a vertebral body may become severely damaged due to tumor or trauma. The vertebral body may be removed along with the adjacent intervertebral discs to on both sides. A cage typically may be put in place in the region formerly occupied by the vertebral body and the adjacent intervertebral discs. The cage must be secured between the adjacent superior and inferior vertebral bodies by compression and supplemental fixation to promote successful bone fusion.

One approach to secure the cage between the vertebral bodies may include a rigid system of screws and rods on a posterior aspect of the spine. The screws may be inserted into the pedicles of the vertebrae where the bone includes mostly cortical material to act as bone anchors, and the rods may be inserted into heads of the screws. Two rods may run substantially parallel to the spine and secure the spine in the desired shape and curvature. Instruments may be used to compress the attached vertebrae together to tightly grip the cage between them. Another approach to secure the cage between the vertebral bodies includes screws and rods on a lateral or anterior aspect of the spine. Yet another approach includes a Kaneda-style lateral plate.

SUMMARY

An apparatus for coupling with a fixation rod to allow spinal compression, distraction, and fixation along an antero-lateral aspect of a spine includes an elongated plate, first and second fixation screws, and a first arm. The elongated plate includes a first aperture at a superior end and a second aperture at an inferior end. The first fixation screw is received by the first aperture and engages a first body portion of a first vertebra. The second fixation screw is received by the second aperture and engages a second body portion of a second vertebra. The first arm extends transversely from a first base portion on the elongated plate and includes a first hook to couple with a first portion of the fixation rod.

In other features, a second arm spaced extends transversely from a second base portion on the elongated plate and includes a second hook to couple with a second portion of the fixation rod.

In yet other features, the apparatus is combined with the fixation rod and further includes a first bone screw to attach to the first body portion and receive the first portion of the fixation rod and a second bone screw to attach to the second body portion and receive the second portion of the fixation rod.

In yet other features, a first capture screw is configured to capture the first portion of the fixation rod within the first hook.

In yet other features, a first slot in the plate is configured to slidably receive the first based portion of the first arm. In still other features, the first base portion of the first arm includes a first aperture for receiving a first locking bolt and the first slot includes a T-shaped cross-sectional profile configured to slidably receive the first locking bolt and a first locking nut. In still other features, the first locking bolt and the first locking nut are configured to compress the first base portion against the plate to lock the first base portion in a first position.

In yet other features, an integral locking mechanism extends into the first aperture and includes an elastically flexible projection to prevent rotation of the first fixation screw relative to the plate.

In yet other features, a first staple received by the first bone screw includes a first attachment element configured to pierce the first body portion. A second staple received by the second bone screw includes a second attachment element configured to pierce the second body portion. Each of the first and second attachment elements includes at least one of spikes, cleats, protrusions, and projections.

An apparatus for coupling with a fixation rod to allow spinal compression, distraction, and fixation along an antero-lateral aspect of a spine includes an elongated plate, a first fixation screw, a second fixation screw, a first arm, and a second arm. The elongated plate includes a first aperture at a superior end and a second aperture at an inferior end. The first fixation screw is received by the first aperture and is configured to engage a first body portion of a first vertebra. The second fixation screw is received by the second aperture and is configured to engage a second body portion of a second vertebra. The first arm extends transversely from a first base portion on the elongated plate and includes a first hook to couple with a first portion of the fixation rod. The second arm extends transversely from a second base portion on the elongated plate and includes a second hook to couple with a second portion of the fixation rod.

In other features, a first slot in the plate is configured to slidably receive the first based portion of the first arm. The first base portion of the first arm includes a first aperture for receiving a first locking bolt and the first slot includes a T-shaped cross-sectional profile configured to slidably receive the first locking bolt and a first locking nut. The first locking bolt and the first locking nut are configured to compress the first base portion against the plate to lock the first base portion a first position. A second slot in the plate is configured to slidably receive the second based portion of the second arm.

A system for spinal compression, distraction, and fixation along an antero-lateral aspect of a spine includes an elongated plate, a first fixation screw, a second fixation screw, a fixation rod, a first bone screw, a second bone screw, a first arm, and a second arm. The elongated plate includes a first aperture at a superior end and a second aperture at an inferior end. The first fixation screw is received by the first aperture and is configured to engage a first body portion of a first vertebra. The second fixation screw is received by the second aperture and is configured to engage a second body portion of a second vertebra. The fixation rod includes a first portion at a superior end and second portion at an inferior end. The first bone screw is configured to attach to the first body portion and is configured to receive the first portion of the fixation rod. The second bone screw is configured to attach to the second body portion and is configured to receive the second portion of the fixation rod. The first arm extends transversely from a first base portion on the elongated plate and includes a first hook to couple with the first portion of the fixation rod. The second arm extends transversely from a second base portion on the elongated plate and includes a second hook to couple with the second portion of the fixation rod.

In other features, the elongated plate is configured to be provisionally coupled with the fixation rod by first and second capture screws of the first and second hooks to pivot away from the first and second vertebrae.

In yet other features, a first slot in the plate is configured to slidably receive the first base portion of the first arm. The first base portion of the first arm includes a first aperture for receiving a first locking bolt and the first slot includes a T-shaped cross-sectional profile configured to slidably receive the first locking bolt and a first locking nut. The first locking bolt and the first locking nut are configured to compress the first base portion against the plate to lock the first base portion a first position.

DETAILED DESCRIPTION

The purpose of this invention is to allow the surgeon to insert bone screws, a rod, and set screws laterally to be used for compression and distraction of the affected disc space. The distraction or compression can be held by locking down the set screws onto the rod and bone screw. The surgeon can then do the disc removal or any disc prep needed. The cage is then inserted. The set screws are loosened on the rod and bone screws allowing the surgeon to compress the superior and inferior vertebral bodies down onto the corpectomy cage. The mating plate is then attached to the rod between the bone screws and rotated until it touches the vertebral bodies. The connection between the plate and the rod is tightened and screws are inserted through the plate for attachment to the vertebral bodies.

Embodiments of the invention will now be described with reference to the Figures, wherein like numerals reflect like elements throughout. The terminology used in the description presented herein is not intended to be interpreted in any limited or restrictive way, simply because it is being utilized in conjunction with detailed description of certain specific embodiments of the invention. Furthermore, embodiments of the invention may include several novel features, no single one of which is solely responsible for its desirable attributes or which is essential to practicing the invention described herein. The words proximal and distal are applied herein to denote specific ends of components of the instrument described herein. A proximal end refers to the end of an instrument nearer to an operator of the instrument when the instrument is being used. A distal end refers to the end of a component further from the operator and extending towards the surgical area of a patient and/or the implant.

An exemplary system for spinal compression, distraction, and fixation illustrated in FIGS. 1-7 includes at least two staples, two bone screws, a rod, two set screws, a lateral plate, two fixation screws, and two capture screws. The staples give better stability to the bone surrounding the implanted bone screw. The bone screws allow for compression and distraction of the disc space and provide medial/lateral stability. The rod provides stability of construct in medial/lateral direction. The set screws lock down the rod to the bone screws. The lateral plate provides medial/lateral stability and anterior/posterior stability and attachment to the rod. The fixation screws provide attachment of the lateral plate to the vertebral body. The capture screw provides attachment of the lateral plate to the rod. The bone screw attaches the construct to the vertebral bodies. The rod attaches to the bone screws and allows for compression and distraction of the disc space.

Figure 7:
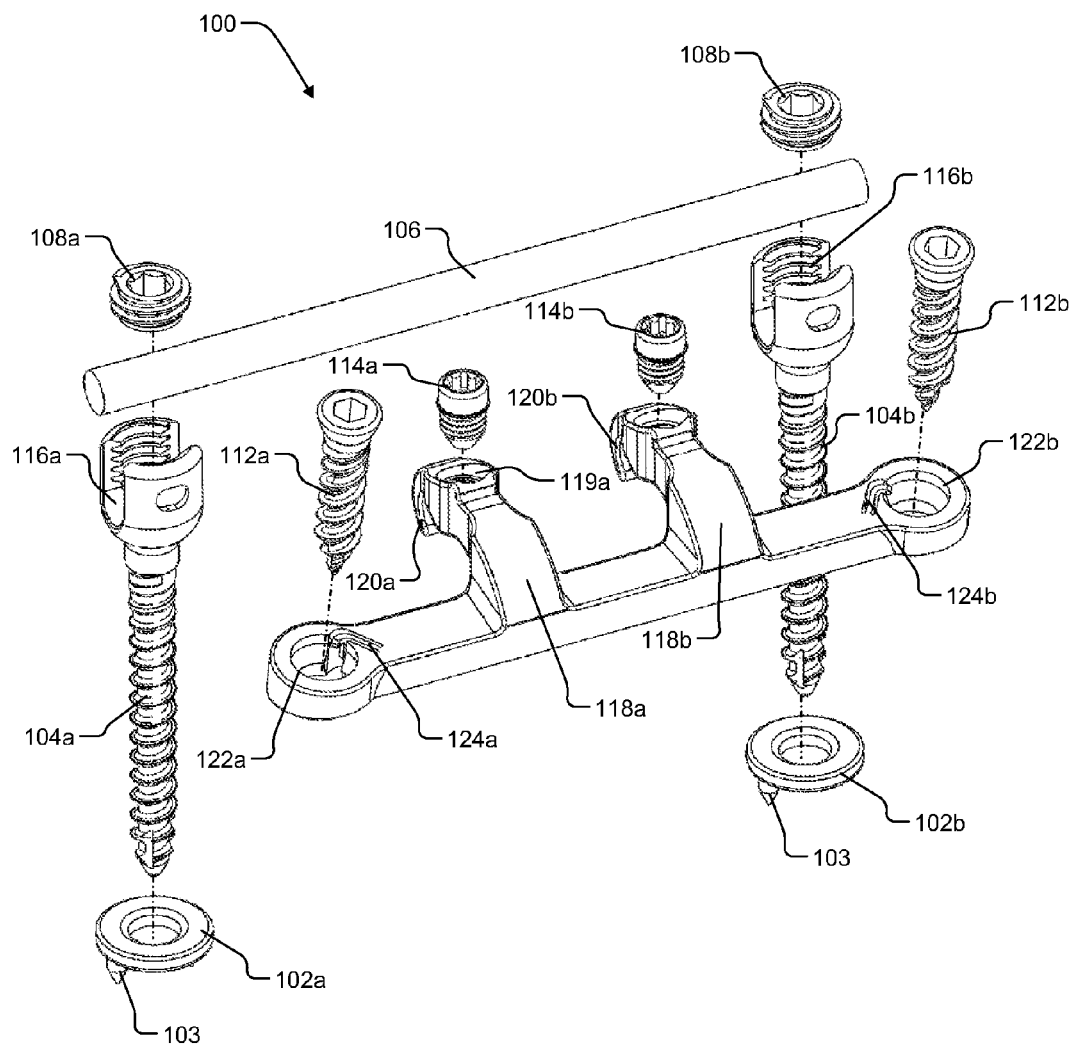
FIG. 7 is an exploded perspective view of the exemplary system for spinal compression, distraction, and fixation according to the principles of the present disclosure.

Referring now to FIG. 7, a system 100 for compression, distraction, and fixation of the vertebrae from an antero-lateral approach comprises two staples 102a/b, two bone screws 104a/b, a rod 106, two set screws 108a/b, a lateral plate 110, two fixation screws 112a/b, and two capture screws 114a/b. The system 100 may be attached to first and second vertebrae V1 and V2 (not shown) from a lateral or antero-lateral approach to the spine. The plate 110 may provide for rigid fixation of the attached vertebrae while the bone screws 104 and rod 106 may provide for compression/distraction capability using various other instruments.

The staples 102a/b may be attached to the vertebrae V1/V2 respectively and provide greater stability to receive the bone screws 104a/b. Each of the staples 102a/b may include one or more spikes, cleats, protrusions, projections, or other attachment elements 103. Each of the staples 102a/b may include an aperture to receive a bone screw 104. Once the bone screws 104 have been inserted through the staples 102a/b, the rod 106 may be inserted into rod-receiving portions 116a/b of the screws 104/ab. Set screws 108a/b may subsequently be used to secure the rod 106 within the rod-receiving portions 116a/b. Prior to final tightening of the set screws 108a/b, the bone screws 104a/b may be used as anchoring points for various compression and distraction instruments to pull apart or bring together the attached vertebrae V1/V2.

The plate 110 may be coupled to the rod 106 using cantilevered arms 118a/b. Each of the arms 118a/b may be integral with plate 110. Each of the arms 118a/b may terminate in a hook 120a/b configured to extend at least partially around the rod 106. The arms 118a/b may include apertures 119 to receive the capture screws 114a/b to secure the hooks 120a/b to the rod 106. Thus, the plate 110 may be loosely secured to the rod 106 as instruments compress or distract the vertebrae via the bone screws 104a/b.

Upon completion of the compression or distraction, the plate 110 may be rigidly secured to the rod 106 by tightening the capture screw 114a/b. The plate 110 may also be secured to the vertebrae V1/V2 using the fixation screws 112a/b within apertures at either end of the lateral plate 110. For example, the plate 110 may include a substantially elongated plate having opposite ends configured for attachment to adjacent vertebrae such as vertebrae V1/V2. The plate 110 may include apertures 122a/b that receive the fixation screws 112a/b. Integral locking mechanisms 124a/b may include flexible projections that extend partially into the apertures 122a/b. As the fixation screws 112a/b pass through the apertures 122a/b, the locking mechanisms 124a/b may flex away from the apertures 122a/b to permit the screws 112a/b to pass therethrough. Once the screws 112a/b are fully seated within the apertures 122a/b, the locking mechanisms 124a/b may elastically return to extend partially into the apertures 122a/b to prevent the screws 112a/b from backing out relative to the plate 110.

It can be understood that elements of the exemplary systems and methods of the present disclosure may engage across multiple levels of the spine according to the principles of the present disclosure. For example, the system 100 may include a length to span from a first level vertebral body to a third level vertebral body skipping one level that has been removed by a vertebrectomy procedure. The system 100 may require only first screws 104a and 112a on the first level and second screws 104b and 112b on the third level while the rod 106 and plate 110 span the open space between. This system 100 may be used to compress a cage within the space of the second level vertebral body that has been removed. In other examples, the system 100 may include a length to span from a first level vertebral body to a fourth level vertebral body skipping two levels that have been removed by a vertebrectomy procedure. Thus, the length of the system 100 may such to conform to a variety of procedures and patient anatomies.

Further, it can be understood that elements of the exemplary systems and methods of the present disclosure may be repeated as required to provide sufficient strength and placement flexibility according to the principles of the present disclosure. For example, the system 100 may include more than two bone screws 104, staples 102, and/or fixation screws 112 to attach to more than two levels of vertebral bodies. The plate 110 may include more than two arms 114 to couple with the fixation rod 106.

Figure 1:
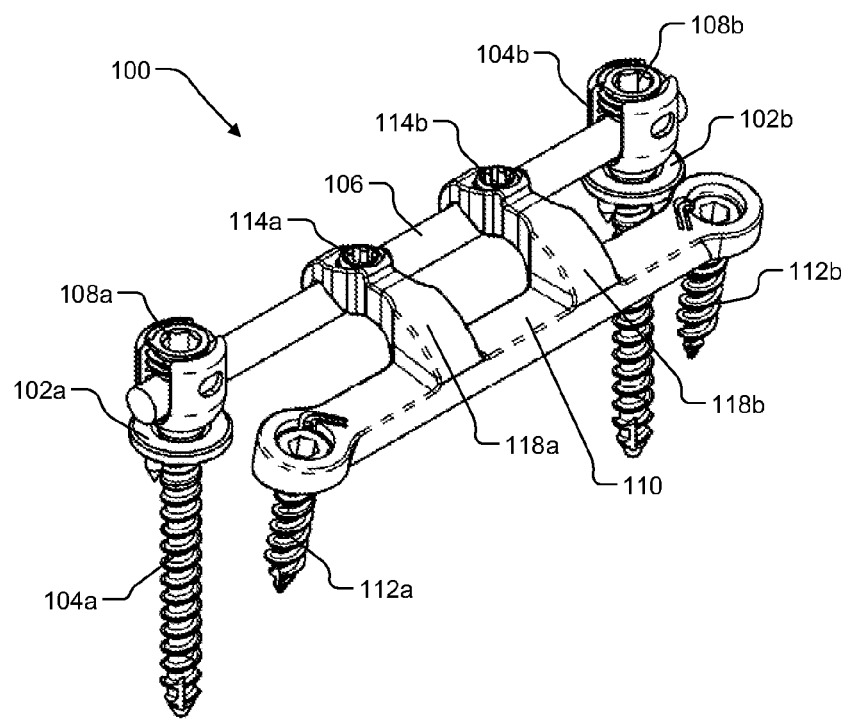
FIG. 1 is a perspective view of an exemplary system for spinal compression, distraction, and fixation according to the principles of the present disclosure.
Figure 2:
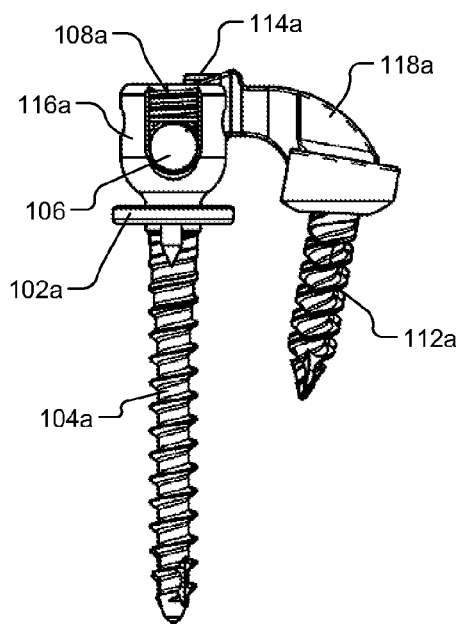
FIG. 2 is a side view looking into a longitudinal axis of a rod the exemplary system for spinal compression, distraction, and fixation according to the principles of the present disclosure.
Figure 3:
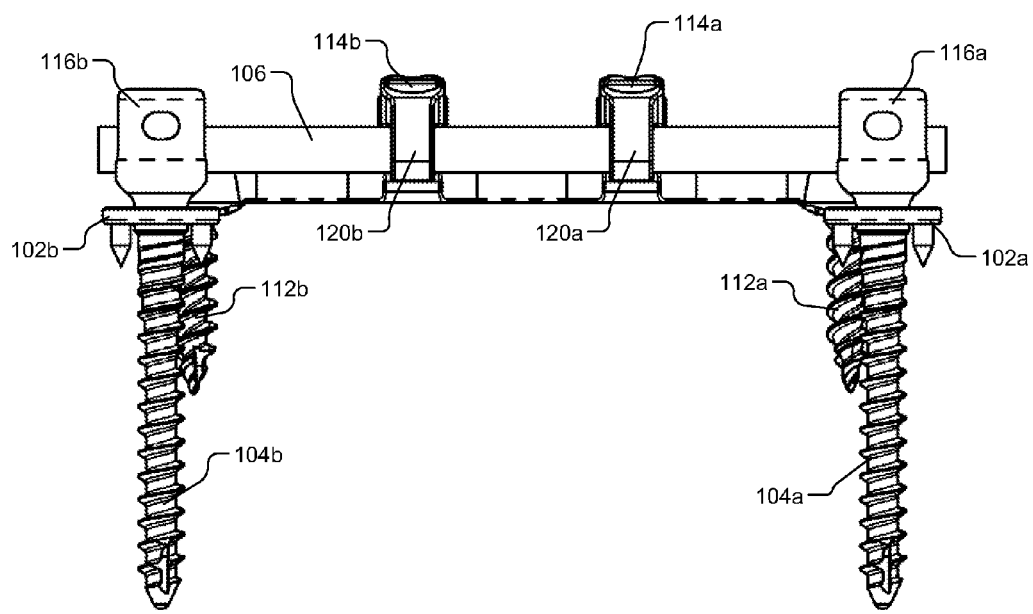
FIGS. 3 and 4 are side views along the longitudinal axis of the rod of the exemplary system for spinal compression, distraction, and fixation according to the principles of the present disclosure.
Figure 4:
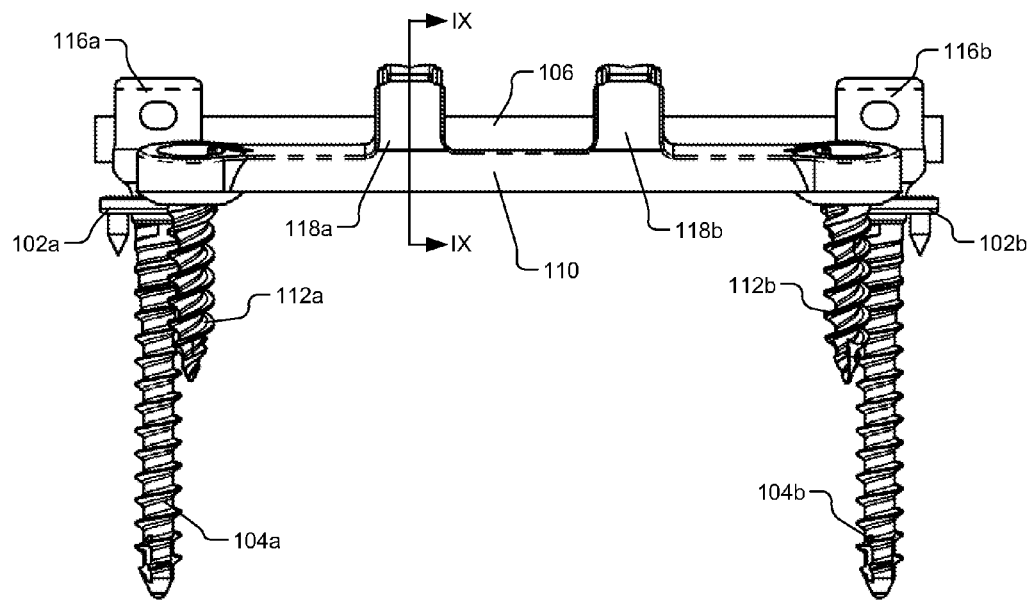
Figure 5:
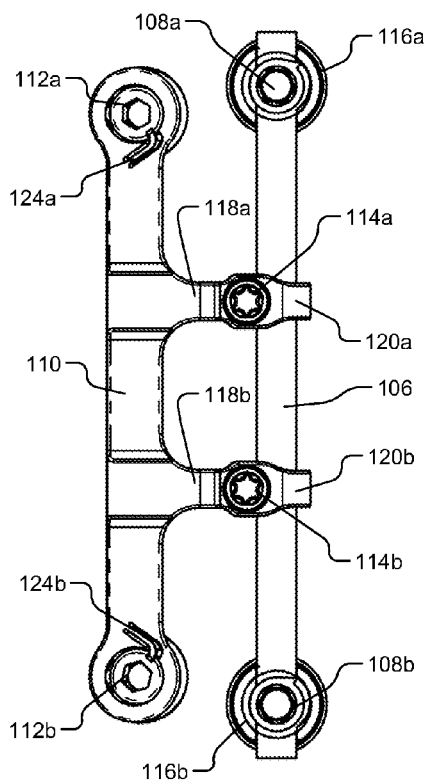
FIGS. 5 and 6 are top and bottom views of the exemplary system for spinal compression, distraction, and fixation according to the principles of the present disclosure.
Figure 6:
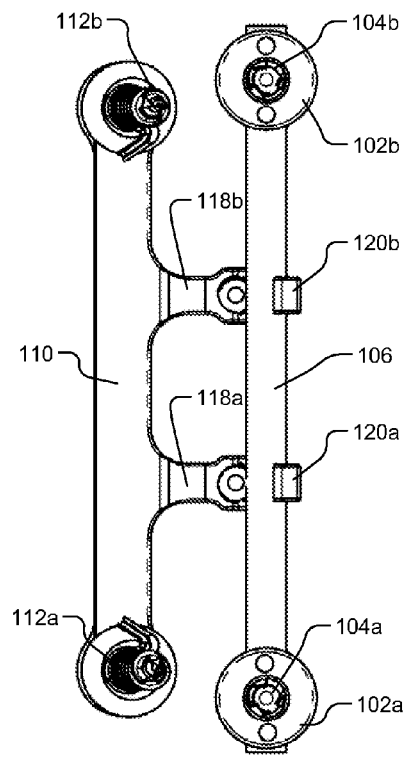
Figure 8:
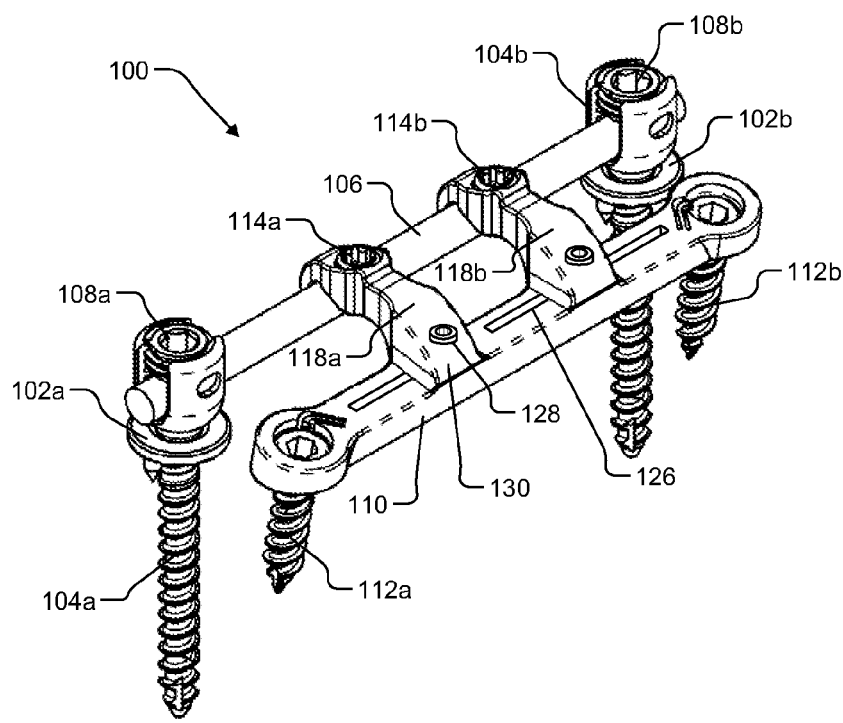
FIG. 8 is a perspective view of another exemplary system for spinal compression, distraction, and fixation according to the principles of the present disclosure.
Figure 9:
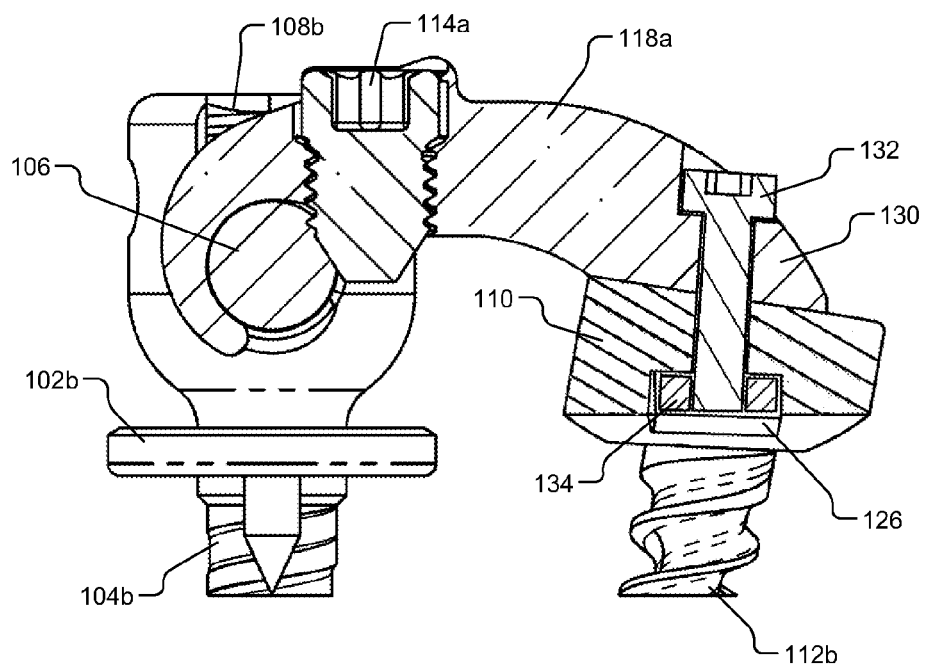
FIG. 9 is a partial cross-sectional view of the exemplary system of FIG. 8 looking into a similarly located plane as plane IX of the exemplary system in FIG. 4.

Alternately, as shown in FIG. 8 and in the cross-sectional view of FIG. 9, one or more slots 126 may be provided within the plate 110 to permit sliding of the arms 118a and/or 118b along the length of the system 100. The slot 126 may slidably engage with a locking mechanism 128 that extends through a base portion 130 of the arm 118a. For example, the slot 126 may include a generally inverted T-shaped cross-sectional profile. The locking mechanism 128 may include a bolt 132 and nut 134. The bolt 132 and nut 134 may be tightened to clamp the base portion 130 of the arm 118a to the plate 110. The bolt 132 may be locked in place by similar integral locking mechanisms as illustrated in FIG. 5.

Example embodiments of the methods and systems of the present invention have been described herein. As noted elsewhere, these example embodiments have been described for illustrative purposes only, and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments, but should be defined only in accordance with the following claims and their equivalents.

The invention claimed is:

1. A system for spinal compression, distraction, and fixation along an antero-lateral aspect of a spine, comprising:
   an elongated plate including a first aperture at a superior end and a second aperture at an inferior end;
   a first fixation screw received by the first aperture and configured to engage a first body portion of a first vertebra;
   a second fixation screw received by the second aperture and configured to engage a second body portion of a second vertebra;
   a fixation rod including a first portion at a superior end and a second portion at an inferior end;
   a first bone screw configured to attach to the first body portion and configured to receive a first longitudinal length of the fixation rod;
   a second bone screw configured to attach to the second body portion and configured to receive a second longitudinal length of the fixation rod;
   a first arm extending transversely from a first base portion on the elongated plate, the first arm including a first rod passage, the first rod passage defining a first hook, the first rod passage extending along a first axis, the first axis being generally orthogonal to a longitudinal axis of the first arm and generally parallel to a longitudinal axis of the elongated plate, the first hook configured to couple with the first longitudinal length of the fixation rod; and a second arm spaced extending transversely from a second base portion on the elongated plate, the second arm including a second rod passage, the second rod passage defining a second hook, the second rod passage extending along a second axis coaxial to the first axis, wherein the apparatus is configured to couple with the second longitudinal length of the fixation rod.

2. The system of claim 1, wherein the elongated plate is configured to be provisionally coupled with the fixation rod by first and second capture screws of the first and second hooks to pivot away from the first and second vertebrae.

3. The system of claim 1, further comprising a first slot in the plate configured to slidably receive the first base portion of the first arm.

4. The system of claim 3, wherein first base portion of the first arm includes a first aperture for receiving a first locking bolt and the first slot includes a T-shaped cross-sectional profile configured to slidably receive the first locking bolt and a first locking nut.

5. The system of claim 4, wherein the first locking bolt and the first locking nut are configured to compress the first base portion against the plate to lock the first base portion a first position.

\* \* \* \* \*